(12) United States Patent
Brose et al.

(10) Patent No.: US 11,793,260 B2
(45) Date of Patent: Oct. 24, 2023

(54) SKULL MOUNTING SYSTEM FOR HEADGEAR, RESPIRATORY HOOD WITH HEADGEAR AND METHOD FOR FASTENING OF HEADGEAR

(71) Applicant: SATA GmbH & Co. KG, Kornwestheim (DE)

(72) Inventors: Jens Brose, Ottmarsheim (DE); Marco Schönemann, Wendlingen (DE)

(73) Assignee: SATA GmbH & Co. KG, Kornwestheim (DE)

( * ) Notice: Subject to any disclaimer, the term of this patent is extended or adjusted under 35 U.S.C. 154(b) by 102 days.

(21) Appl. No.: 17/394,741

(22) Filed: Aug. 5, 2021

(65) Prior Publication Data
US 2022/0039502 A1 Feb. 10, 2022

(30) Foreign Application Priority Data
Aug. 7, 2020 (DE) .................. 10 2020 120950.9

(51) Int. Cl.
*A42B 3/08* (2006.01)
*A42B 3/14* (2006.01)
*A61F 9/06* (2006.01)

(52) U.S. Cl.
CPC ............. *A42B 3/085* (2013.01); *A42B 3/145* (2013.01); *A61F 9/06* (2013.01)

(58) Field of Classification Search
CPC ......... A42B 3/085; A42B 3/145; A42B 3/142; A42B 3/08; A61F 9/06; A62B 18/08
See application file for complete search history.

(56) References Cited

U.S. PATENT DOCUMENTS

| | | | |
|---|---|---|---|
| 1,153,907 | A | 9/1915 | Halbert |
| 1,170,052 | A | 2/1916 | Diemer |
| 2,739,309 | A | 3/1956 | Frieder |
| 2,796,609 | A | 6/1957 | Fisher |
| 2,879,513 | A | 3/1959 | Hornickel |
| 2,921,318 | A | 1/1960 | Voss |

(Continued)

FOREIGN PATENT DOCUMENTS

| | | |
|---|---|---|
| CN | 2820148 Y | 9/2006 |
| DE | 3543341 A1 | 9/1986 |

(Continued)

OTHER PUBLICATIONS

European Search Report for European Patent Application No. 21188233.7, dated Jan. 5, 2022.

(Continued)

*Primary Examiner* — Khaled Annis
(74) *Attorney, Agent, or Firm* — Paul D. Bianco; Stephen Bongini; Fleit Intellectual Property Law

(57) ABSTRACT

A skull mounting system for headgear, preferably for a respirator hood, is described. The skull mounting system comprises a headband with a front head strap, which extends around the front of the head of a wearer, and a rear head strap, which is found on the back of the head of the wearer. The rear head strap is connected to the front head strap by means of two swivel joints. The swivel joints are at least partially freely rotatable in a corresponding adjustment position and are not rotatable in a corresponding locked position.

20 Claims, 5 Drawing Sheets

(56) References Cited

U.S. PATENT DOCUMENTS

| | | | | |
|---|---|---|---|---|
| 3,075,201 A | * | 1/1963 | Lindblom | A61F 9/06 2/8.1 |
| 3,555,560 A | | 1/1971 | Rascke | |
| 3,696,442 A | * | 10/1972 | Amundsen | A61F 9/06 2/8.1 |
| 3,994,023 A | | 11/1976 | Aileo | |
| 4,464,800 A | * | 8/1984 | Edwards | A61F 9/06 2/451 |
| 4,619,254 A | | 10/1986 | Moretti | |
| 4,621,377 A | | 11/1986 | Pennell | |
| 4,888,831 A | | 12/1989 | Oleson | |
| D316,164 S | | 4/1991 | Furthbauer | |
| 5,150,479 A | | 9/1992 | Oleson | |
| 5,319,808 A | | 6/1994 | Bishop | |
| 5,608,917 A | | 3/1997 | Landis | |
| 5,898,949 A | | 5/1999 | Barthold | |
| 6,081,931 A | | 7/2000 | Burns | |
| D484,436 S | | 12/2003 | Laundry | |
| D501,956 S | | 2/2005 | Grepper | |
| 8,336,114 B1 | * | 12/2012 | Lee | A42B 3/145 2/9 |
| 8,505,121 B2 | | 8/2013 | Ahigren | |
| 9,113,671 B2 | | 8/2015 | Pfanner | |
| 10,588,373 B2 | * | 3/2020 | Staudinger | A42B 3/08 |
| 11,013,289 B1 | | 5/2021 | Lucero | |
| 11,096,439 B2 | | 8/2021 | King | |
| 2006/0156448 A1 | | 7/2006 | Garneau | |
| 2007/0245466 A1 | | 10/2007 | Lilenthal | |
| 2007/0245467 A1 | * | 10/2007 | Lilenthal | A42B 3/225 2/416 |
| 2008/0109947 A1 | | 5/2008 | Dubois | |
| 2010/0050325 A1 | | 3/2010 | Wang-Lee | |
| 2010/0229286 A1 | * | 9/2010 | Ahlgren | A42B 3/142 2/416 |
| 2010/0235971 A1 | | 9/2010 | Ahlgren | |
| 2011/0265254 A1 | * | 11/2011 | Ma | A61H 7/006 2/420 |
| 2011/0289659 A1 | * | 12/2011 | Lanez | A42B 3/145 2/411 |
| 2012/0144565 A1 | | 6/2012 | Huh | |
| 2013/0111653 A1 | | 5/2013 | Huh | |
| 2013/0219596 A1 | | 8/2013 | Carvell | |
| 2013/0239303 A1 | | 9/2013 | Cotterman | |
| 2014/0101828 A1 | | 4/2014 | Sugerman | |
| 2015/0059066 A1 | | 3/2015 | Ketterer | |
| 2015/0143618 A1 | | 5/2015 | Pereira | |
| 2015/0143669 A1 | | 5/2015 | Pereira | |
| 2015/0250251 A1 | | 9/2015 | Ahlgren | |
| 2015/0359677 A1 | * | 12/2015 | Sommers | A42B 3/225 2/8.2 |
| 2016/0183622 A1 | * | 6/2016 | Patel | A42B 3/222 2/424 |
| 2016/0249701 A1 | | 9/2016 | Xiong | |
| 2016/0262484 A1 | | 9/2016 | Huh | |
| 2016/0331059 A1 | | 11/2016 | Basson | |
| 2016/0361201 A1 | * | 12/2016 | Sommers | A42B 3/06 |
| 2017/0112221 A1 | | 4/2017 | Gotti | |
| 2017/0112223 A1 | | 4/2017 | Gotti | |
| 2017/0150771 A1 | | 6/2017 | Huh | |
| 2017/0238643 A1 | * | 8/2017 | Pereira | A42B 3/14 |
| 2017/0245578 A1 | | 8/2017 | Xiong | |
| 2017/0255027 A1 | * | 9/2017 | Hofer-Kraner | A61F 9/067 |
| 2019/0029355 A1 | * | 1/2019 | Seo | A61F 9/06 |
| 2019/0141847 A1 | | 5/2019 | Chang | |
| 2020/0022443 A1 | | 1/2020 | Wetzel | |
| 2020/0390182 A1 | * | 12/2020 | Huh | A42B 3/14 |
| 2021/0037905 A1 | | 2/2021 | Ward | |
| 2021/0120904 A1 | | 4/2021 | Kühnlein | |
| 2021/0337909 A1 | | 11/2021 | Tolk | |
| 2021/0337911 A1 | | 11/2021 | Franke | |
| 2021/0378868 A1 | * | 12/2021 | Huh | A61F 9/06 |
| 2022/0039499 A1 | | 2/2022 | Brose | |
| 2022/0039502 A1 | * | 2/2022 | Brose | A42B 3/085 |
| 2022/0071334 A1 | * | 3/2022 | Huang | A42B 3/222 |

FOREIGN PATENT DOCUMENTS

| | | |
|---|---|---|
| DE | 102012000370 A1 | 8/2013 |
| EP | 2123182 A2 | 11/2009 |
| EP | 2207443 B1 | 9/2011 |
| EP | 3568031 A1 | 11/2019 |
| EP | 3815560 A1 | 5/2021 |
| GB | 2098459 A | 11/1982 |
| GB | 2098459 B | 11/1982 |
| JP | 5899836 A | 4/2016 |
| JP | 5899836 B2 | 4/2016 |
| KR | 101932245 B1 | 12/2018 |
| WO | 2009/048794 A1 | 4/2009 |
| WO | 2020/111286 A1 | 6/2020 |
| WO | 2021/216082 A1 | 10/2021 |

OTHER PUBLICATIONS

European Search Report for European Patent Application No. 21188232.9, dated Jan. 4, 2022.
German Search Report dated May 28, 2021 for DE 10 2020 120 950.9 (8 pages).
German Search Report dated May 28, 2021 for DE 20 2020 104 596.2 (8 pages).
For U.S. Appl. No. 17/394,902: Office Action dated Feb. 1, 2023 Response filed May 1, 2023.
Final Office Action dated May 31, 2023, for U.S. Appl. No. 17/394,902.

* cited by examiner

SKULL MOUNTING SYSTEM FOR HEADGEAR, RESPIRATORY HOOD WITH HEADGEAR AND METHOD FOR FASTENING OF HEADGEAR

FIELD OF THE DISCLOSURE

The disclosure relates to a skull mounting system for headgear, preferably a respiratory hood, comprising a headband with a front head strap, which extends around the front of the head of the wearer and a rear head strap, which is found on the back of the head of the wearer, wherein the rear head strap is connected to the front head strap via two swivel joints.

The disclosure also relates to a respiratory hood with such a skull mounting system, as well as a method for fastening headgear to such a skull mounting system.

BACKGROUND

Such skull mounting systems serve for fastening headgear, for example, a respiratory hood, a welder's helmet or a protective helmet on the head of a wearer, and thus form the connection element between the head of the user and the headgear. Such a skull mounting system generally consists of several parts, in which it is advantageous with respect to the adjustment to the head of the wearer if the angle of a rear part of the skull mounting system can be adjusted relative to a front part of the headband, or the head of the wearer. In order to fix the skull mounting system, and therefore the headgear, to the head of the wearer, a length adjustment means is generally provided with which the inner circumference of the skull mounting system can be adjusted. Reducing the inner circumference allows a force fit to be realized between the head of the wearer and the skull mounting system.

A skull mounting system according to the type mentioned above is disclosed, for example, in JP5899836B2. The skull mounting system described there has a front head strap and a rear head strap. These are connected to each other on both sides via swivel joints. Toothing and an opposing mating element are provided on the rear head strap. The front head strap has a pin that is situated in a space between the toothing and the mating element. The space between the toothing and the mating element is smaller than the diameter of the pin in the area of the tips of the toothing. These areas form constrictions to which increased force must be applied during rotation of the swivel joints in order for the pin to overcome the constrictions. A structure that serves to keep the angle of the rear head strap relative to the front head strap in a set position is created by this design.

SUMMARY

One aspect of the disclosure relates to a skull mounting system with adjustable angle between the front head strap and rear head strap, wherein the angle is established with high functional reliability.

Various embodiments are also disclosed herein.

In an embodiment, the skull mounting system according to the disclosure for a headgear, preferably a respiratory hood, includes a headband with a front head strap that extends around the front of the head of the wearer and a rear head strap found on the rear of the head of the wearer. The rear head strap is connected to the front head strap via two swivel joints. The swivel joints are at least partially freely rotatable in a corresponding adjustment position and not rotatable in a corresponding locked position.

Since the swivel joints are not rotatable in the locked position, in contrast to the prior art, it is ensured that the angle position is not adjusted in an undesired manner. This is the case both in the worn state and also in the unworn state. In the worn state, a particularly advantageous force distribution is ensured between the headband and head of the wearer by a non-adjustable angle between the rear head strap and the front head strap. Fastening on the head of the wearer and wearing comfort can thereby be increased. In the unworn state, the angle of fit that the wearer has adjusted is retained, so that readjustment is unnecessary.

It is advantageous for the fastening of the skull mounting system to the head of the wearer if the force on the rear of the head of the wearer acts in the lower region of the back of the head, since the skull mounting system is thereby pulled further downward. This is only possible if the rear head strap is angled downward from the front head strap relative to the head of the wearer, and this angle does not change when the headband is attached to the head of the wearer or is fastened. If the angle were not locked, the rear head strap would move in the direction of the transverse plane during the application of a force passing through the front head strap, which would hinder or prevent the described advantageous force distribution. The locking of the angle between the front head strap and rear band therefore means that the rear head strap does not move up when force is applied.

By locking the angle between the front head strap and the rear head strap, it is also possible to adjust the headband to a variety of head shapes or head sizes and ensure comfortable fit of the headband over long periods.

Both swivel joints can be brought from the adjustment position to the locked position independently of each other.

In terms of improving the wearing comfort, it is particularly advantageous if the front head strap is made from a softer material than the rear head strap. In particular, the front head strap is made from a flexible but shape-stable material that fits snugly against the head. The rear head strap, on the other hand, is made from a less elastic material that is resistant to wear. It is particularly advantageous if the rear head strap has a length adjustment means, which in this case is less susceptible to wear while still ensuring optimal wearing comfort. In particular, in the upper head area an even softer, preferably rubber-elastic, material is provided for this purpose, forming an upper head strap. This upper head strap stabilizes the headgear orthogonally to the head of the wearer or forms an abutment against the downward acting forces that develop due to the weight of the headgear. The skull mounting system therefore consists of three different materials with different hardness and/or elasticity. It is particularly advantageous if the material of the front head strap has a Shore hardness of less than 80 Shore-D, particularly less than 75 Shore-D, and more particularly less than 60 Shore-D.

Such advantageous fastening can be achieved in that the swivel joints can be transferred from the adjustment position to the locked position and back again by a relative movement, particularly by a straight-line relative movement of the axis of rotation of the corresponding swivel joint, preferably by sliding in an elongated hole and/or an elongated groove. During such a relative movement, a rear head strap joint part moves relative to a front head strap-joint part. The rear head strap-joint part are the parts of the swivel joint on the rear head strap and the front head strap-joint part are the parts of the swivel joint on the front head strap. During the relative movement, the position of the axes of rotation relative to the front head strap preferably is not changed, whereas the position of the axes of rotation relative to the rear head strap shifts. As an alternative to a straight-line relative movement, a translatory movement which is not straight-line can also be involved. Through the described shifting of axes of rotation, the swivel joints can be made for the most part in one piece with the front head strap and the rear head strap, so that fewer individual parts are required.

In addition to the parts of the two swivel joints that are made in one piece with the front head strap or the rear head strap, only a clamping connection element is required, in which case the clamping connection element extends through the swivel joint and holds the swivel joint together by abutments on both sides on the connection element. The clamping connection element preferably consists of two individual elements.

It can be particularly advantageous if the swivel joints can be transferred from the locked position to the adjustment position by a relative movement of one part of the corresponding swivel joint on the rear head strap in the viewing direction of the wearer. If the headband is moved back in the opposite direction, the return of the swivel joint to the locked position occurs, whereby the angle of the rear head strap can no longer change relative to the front head strap. Viewing direction is understood to mean the direction in which the wearer looks during the intended use of the skull mounting system or headgear. The viewing direction therefore points from the rear head strap to the front head strap and preferably runs roughly parallel to the front head strap. Locking the corresponding swivel joints relative to the viewing direction ensures that the swivel joint is not automatically moved into the adjustment position when the headgear is worn.

The rear head strap preferably has a length adjustment means via which the length, and therefore inner circumference, of the headband can be adjusted. Shortening the inner circumference allows the headband to be fastened on the head of the wearer, in which case a force from the headband acts on the head of the wearer, leading to a force fit between headband and head. Such a length adjustment means also offers the advantage that the inner circumference of the headband can be adapted to the circumference of the head of the wearer or adjusted.

Each swivel joint can also have a securing means, particularly in the form of a constriction in an elongated groove or elongated hole, which counteracts the transfer of the corresponding swivel joint from the adjustment position to the locked position with a securing force that must be applied in order to overcome the securing means and transfer the swivel joint from the locked position to the adjustment position. Such a securing means ensures that the swivel joints are automatically held in the locked position or the adjustment position even when the skull mounting system is not worn.

A particularly preferred embodiment is one in which the swivel joints each have an angle adjustment means, via which discrete angle adjustments of the rear head strap relative to the front head strap, preferably two or three discrete angle adjustments, are fixedly defined. The angle adjustment means are preferably engaged before the locking means when the swivel joints are transferred from the adjustment position to the locked position. Through this embodiment, a simple means is provided in order to adjust the angle between the rear head strap and the front band reproducibly. It is particularly advantageous if the angle between the front head strap and the rear head strap can be adjusted over a range of 30°, wherein three angle adjustments bare provided.

The angle adjustment means can be formed by elongated pins that protrude from the front head strap and the rear head strap, wherein the front head strap pins are preferably arranged offset in the adjustment position relative to the rear head straps, and wherein the front head strap pins and rear head strap pins engage one in the other in the locked position. Both the front head strap pins and the rear head strap pins can be made in one piece with the headband, which leads to fewer individual parts and facilitates assembly.

It is particularly advantageous if locking means are provided that are formed by toothing, preferably wherein the toothing lies opposite the angle adjustment means with reference to the axis of rotation of the swivel joint. Toothing has the advantage that rotational forces can be taken up particularly well.

In the case of a particularly preferred embodiment example, the swivel joints are arranged essentially in the center between the top and bottom of the front head strap. Optimal fit for different head sizes and head shapes can be achieved by this configuration.

It is advantageous that the swivel joints each have a rotary element that preferably protrudes relative to the front head strap and two intersecting recesses, preferably on the rear head strap. Such rotary elements or such recesses can be made in one piece with the front head strap or the rear head strap, so that fewer individual parts are required.

In this advantageous embodiment, the essentially cylindrical rotary element lies in the locked position within the first recess of the intersecting recesses and in the adjustment position within a second recess of the intersecting recesses. In the adjustment position, the second recess serves as a rotational guide for the rotary element. In a particularly preferred embodiment, the rotary element has two recesses that run along a curved line in the form of an elongated hole, which runs within the rotary element along the outer circumference. These recesses can serve to create an elastic area between recesses and the outer circumference of the rotary element, which yields when the securing means moves over this area when the swivel joints are transferred from the locked position to the adjustment position.

In addition, the swivel joints can each have a rotary element that has outer toothing on the side opposite the rear head strap. In addition, recesses are provided with inner toothing on the side facing the rear head strap, which engage with the outer toothing in the locked position and together form locking means. The force between the front head strap and the rear head strap can be transferred with particular advantage by the toothing.

The swivel joints can each have a rotary element which has a rotary element recess on the side facing the rear head strap. This rotary element recess can accommodate part of the angle adjustment means that protrude on the rear head strap joint part and are pushed into this rotary element recess during transfer of the swivel joints from the locked position to the adjustment position. In this case, at least one side of the rotary element recess forms an end stop for the rotational movement of the corresponding swivel joint when it is rotated into the adjustment position. Such a rotary element recess represents a particularly simple and space-saving means to limit the adjustment of the angle between the front head strap and the rear head strap.

Use of the described skull mounting system is particularly preferred for a respirator hood. Use of a described skull mounting system in this area offers the advantage of improved wear and comfort with maximal adjustment to different head shapes and head sizes.

The method for fastening a described headgear is also considered advantageous. Here the wearer adjusts the angular position of the rear head strap relative to the front head strap according to his or her head shape and/or head size and then transfers the swivel joints via a relative movement, particularly a straight-line relative movement of the swivel joints from the adjustment position to the locked position. The method is particularly useful for the fastening of a respirator hood. The adjustability of the angle between the front head strap and rear head strap is particularly simplified by the described method.

In such a method it is particularly advantageous if the wearer transfers the swivel joints from the adjustment position to the locked position by reducing the length, and therefore the inner circumference, of the headband via the length adjustment means. Adjustment of the rear head strap can therefore occur when the headgear rests on the head of the wearer, in which case it assists the wearer in finding the optimum position of the rear head strap.

BRIEF DESCRIPTION OF THE DRAWINGS

The invention is explained below with reference to embodiment examples. In the figures.

DETAILED DESCRIPTION

Figure 1:
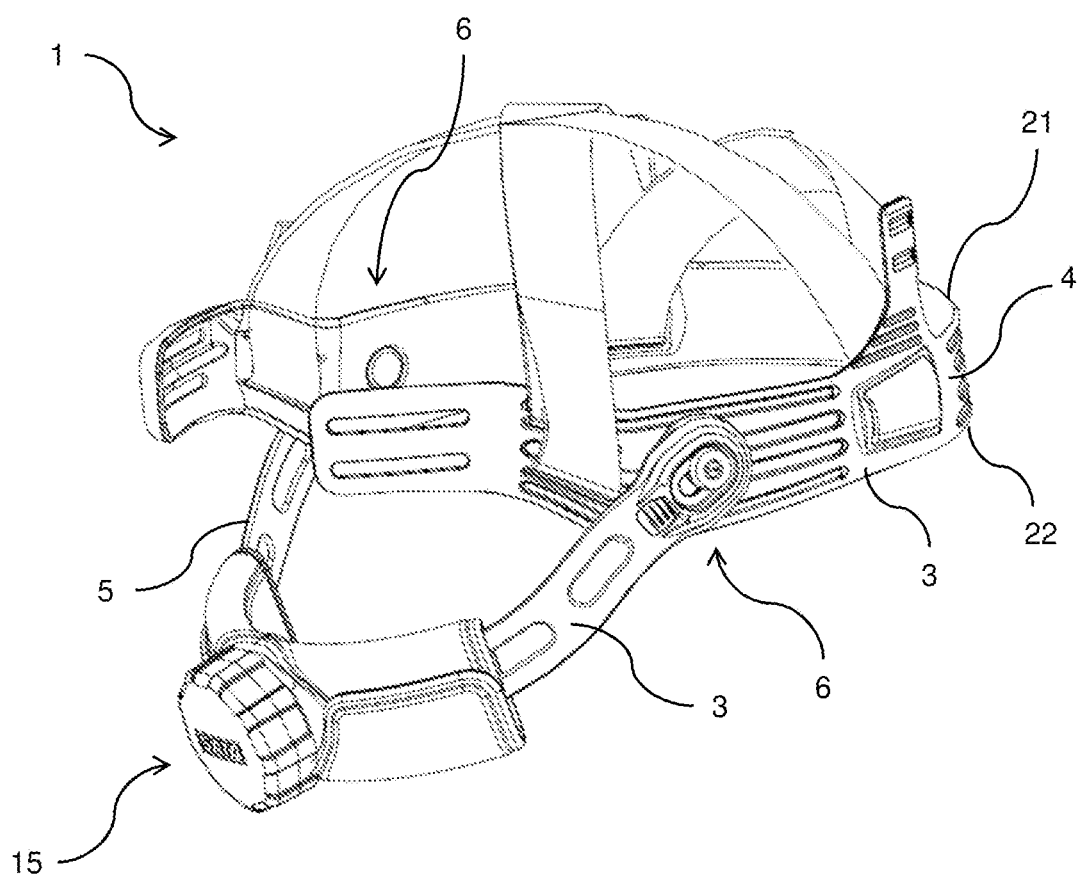
FIG. 1 shows a perspective view of a skull mounting system (for headgear)
Figure 7:
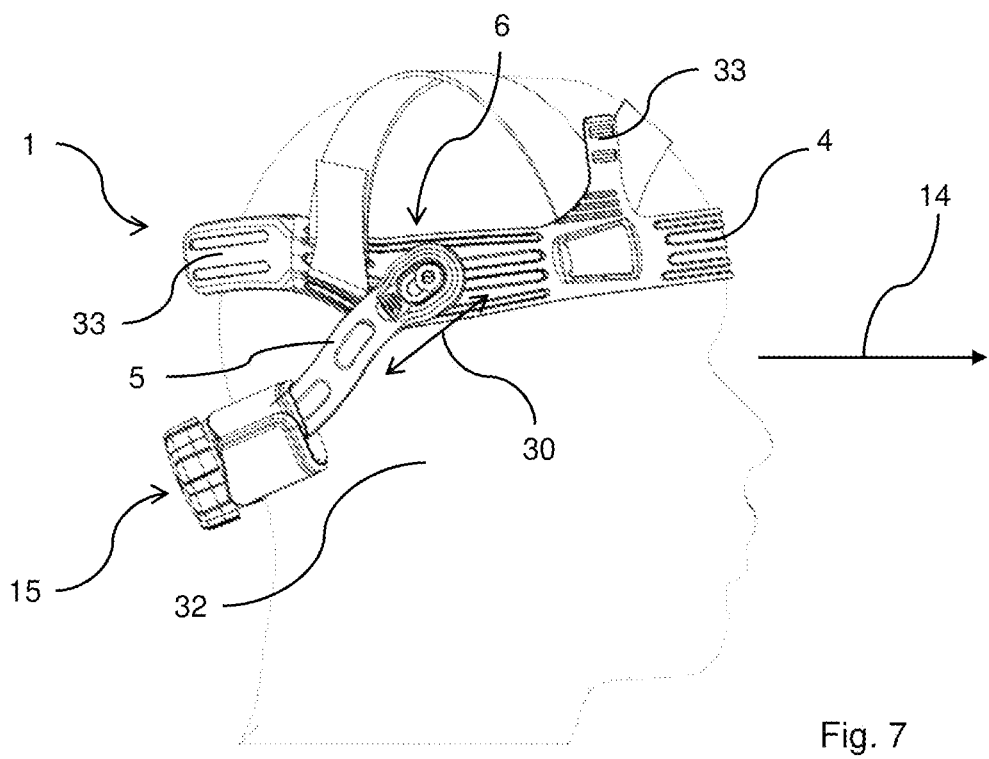
FIG. 7 shows a side view of a skull mounting system for a headgear on the head of a wearer.
Figure 8:
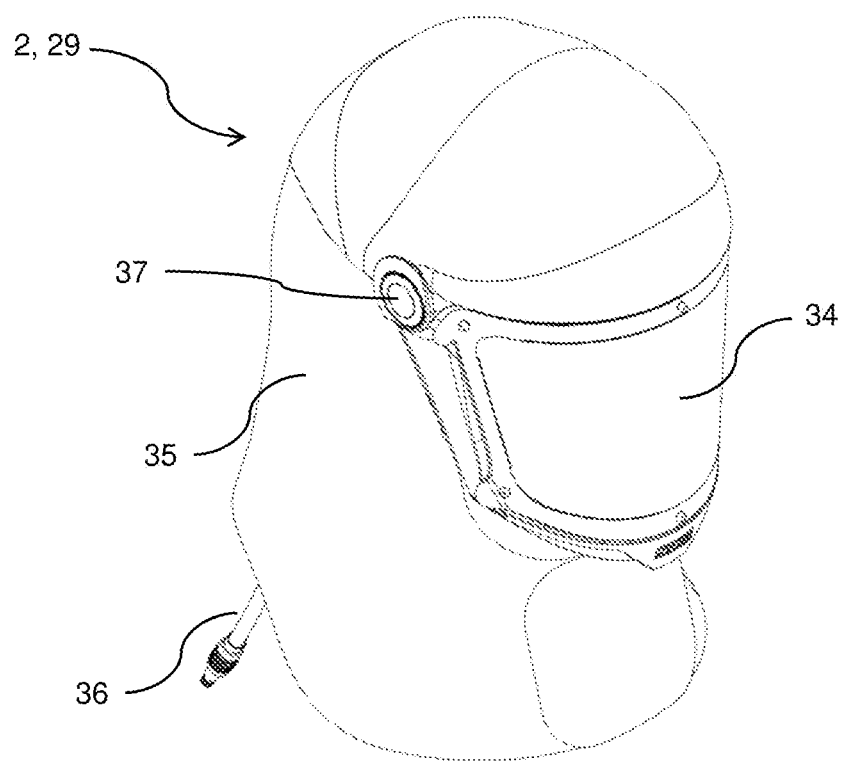
FIG. 8 shows a perspective view of a respiratory hood.

FIGS. 1 and 7 show a skull mounting system 1 for headgear 2 from FIG. 8. The headgear 2 is preferably a respiratory hood, as is also shown in FIG. 8. The skull mounting system 1 includes a headband 3 with a front head strap 4, which extends around the front of the head of a wearer 32, and a rear head strap 5, which is situated on the rear of the head of the wearer, the rear head strap 5 being connected to the front head strap 4 via two swivel joints 6. The swivel joints 6 are at least partially freely rotatable in a corresponding adjustment position 7, depicted in FIGS. 2 and 3, and are not rotatable in a corresponding locked position 8, depicted in FIGS. 4 and 5.

The swivel joint 6 of skull mounting system 1 are essentially arranged in the center between the top 21 and bottom 22 of the front head strap 4.

The rear head strap 5 has a length adjustment means 15, by means of which the length, and therefore the inner circumference, of headband 3 can be adjusted.

Figure 2:
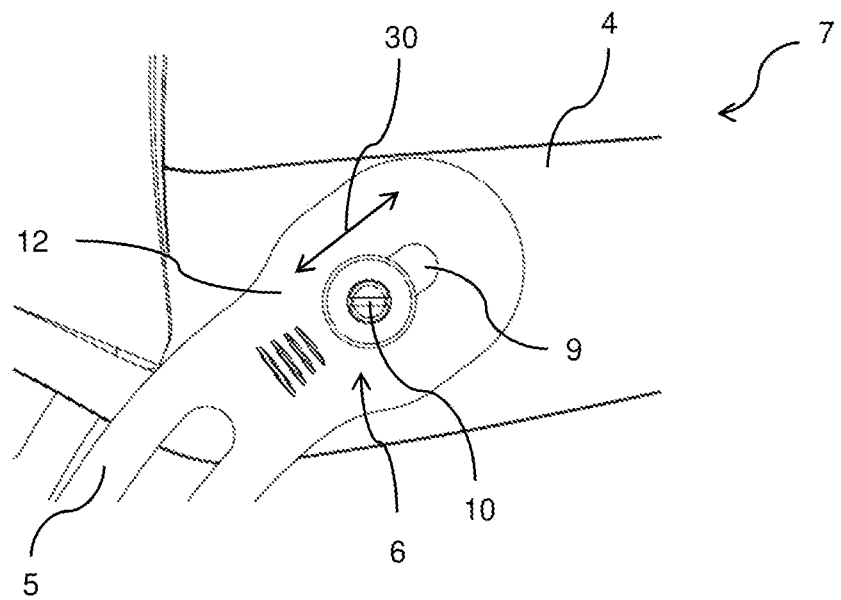
FIG. 2 shows a cut-out view of a swivel joint in the adjustment position.
Figure 3:
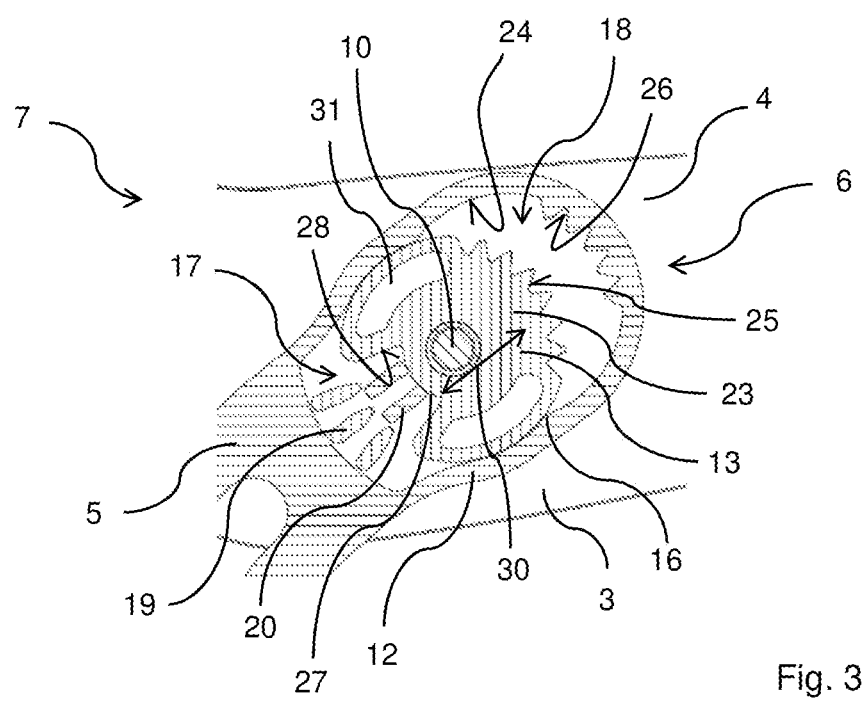
FIG. 3 shows a cut-out sectional view of a swivel joint in the adjustment position.
Figure 4:
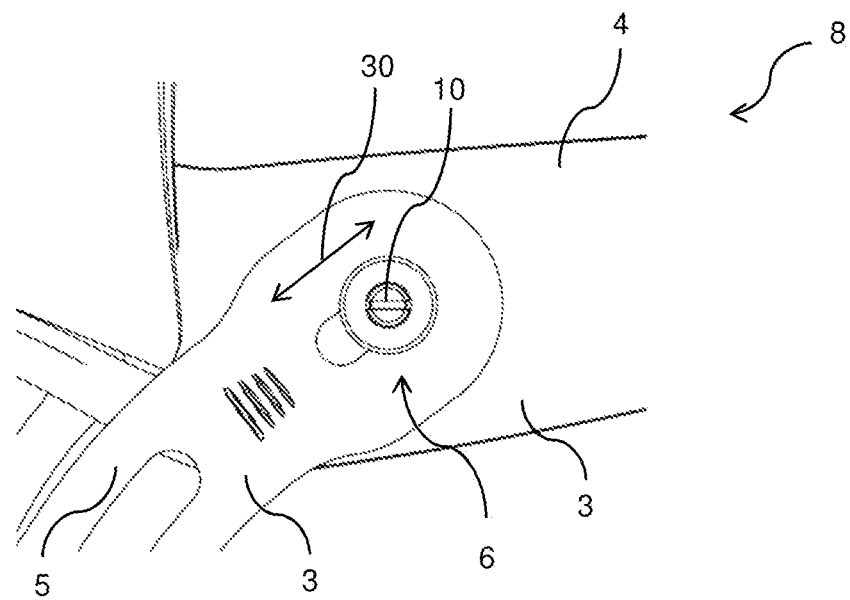
FIG. 4 shows a cut-out view of a swivel joint in the locked position.
Figure 5:
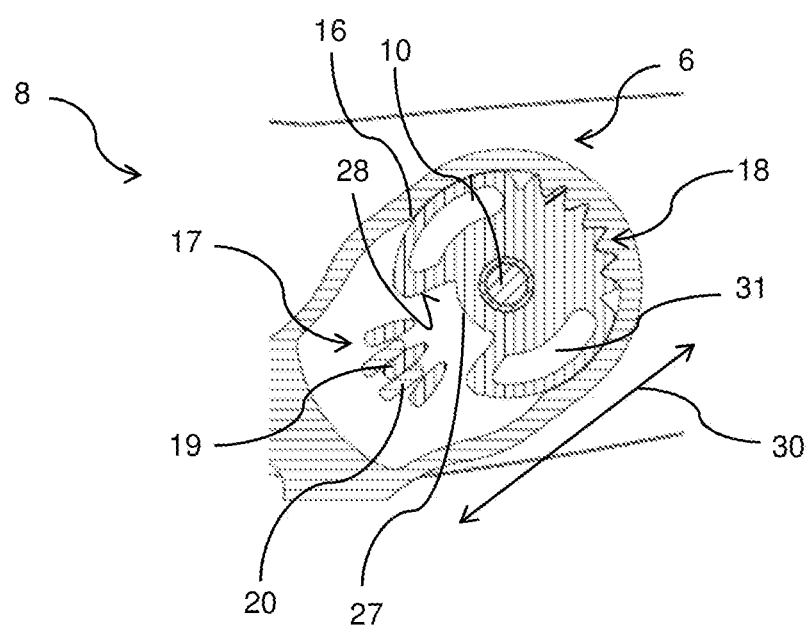
FIG. 5 shows a cut-out sectional view of a swivel joint in the locked position.

The adjustment position 7 is shown in FIGS. 2 and 3, in which the swivel joints 6 are at least partially freely rotatable. FIGS. 4 and 5 show the swivel joint 6 in the locked position 8.

As follows from FIGS. 2 to 5, the swivel joint 6 can be transferred by a straight-line relative movement 30, particularly a straight-line relative movement 30 of the axis of rotation 10 of swivel joint 6, preferably by sliding in an elongated hole 9 and/or an elongated groove, from the adjustment position 7 into the locked position 8 and back. During such a relative movement 30, the rear head strap joint part 12 moves relative to the front head strap joint part 13. The relative movement 30 occurs here preferably approximately along the plane perpendicular to the axis of rotation 10.

The swivel joint 6 can therefore be transferred by a relative movement 30 of part of the corresponding swivel joint 6 on the rear head strap 5 in the viewing direction of wearer 14 shown in FIG. 7 from the locked position 8 into the adjustment position 7.

If headgear 2, particularly the respirator hood 29, is attached to the head of the wearer 32 with a skull mounting system 1, this is done so that the wearer adjusts the angle position of the rear head strap 5 relative to the front head strap 4 according to his head shape and/or his or her head size and then transfers the swivel joint 6 via a relative movement 30, particularly a straight-line relative movement 30 of axis of rotation 10 from the adjustment position 7 into the locked position 8.

The wearer can transfer the swivel joint 6 manually from the adjustment position 7 into the locked position 8. However, this can also be done by reducing the length, and therefore the inner circumference, of the headband 3 via the length adjustment means 15. In this case, the swivel joints 6 are automatically pulled into the locked position 8 by the force resulting from shortening of the headband 3 by means of length adjustment means 15.

To fix the swivel joint 6, the rear head strap 5 as well as the rear head strap-joint part 12 are pushed in the direction of the back of the head of the wearer. This locked position is shown in FIGS. 4 and 5.

FIGS. 3 and 5 show a sectional view of the swivel joint 6 along the plane perpendicular to axis of rotation 10 and passing in the center through rear head strap joint part 12. It is apparent here that the swivel joints 6 each have a securing means 16, particularly in the form of a constriction in a longitudinal groove or a longitudinal hole, which counteracts transfer of the corresponding swivel joint 6 from the adjustment position 7 to the locked position 8 with a securing force that must be applied in order to overcome the securing means 16 and transfer the swivel joint 6 from the locked position 8 into the adjustment position 7.

As is also apparent from FIGS. 3 and 5, the swivel joints 6 in this embodiment example each have rotary element 23, which preferably protrudes relative to the front head strap 4. In addition, two intersecting recesses 24 are provided on the rear head strap 5. These intersecting recesses 24 are approximately circular in this case and intersect so that an area is present between both circular recesses 24 that is narrower than the diameter of the circular recesses 24. This area forms said constriction and the intersections of the peripheries of the circular recesses 24 form the securing means 16.

The rotary element 23 has two recesses 31 that run in the form of an elongated hole along a line that runs concentric to the rotary element within rotary element 23. These recesses 31 serve to form an elastic area between the recesses 31 and the outer circumference of the rotary element 23, which yields when the securing means 16 moves beyond this area.

As is also shown, the rotary element 23 has outside toothing 25 on the side opposite rear head strap 5. Recesses 24 are also provided on the side facing rear head strap 5, which have inside toothing 26, which engages with the outside toothing 25 in the locked position 8, and together form the locking means 18.

It also follows from FIGS. 3 and 5 that the rotary element 23 has a rotary element recess 27 on the side facing the rear head strap 5, which accommodates part of the angle adjustment means 17 in the adjustment position 7, wherein at least one side of the rotary element recess 27 forms an end stop 28 for the rotational movement of the corresponding swivel joint 6.

The angle positions of the rear head strap 5 relative to front head strap 4 are fixedly defined via such angle adjustment means 17. In the depicted example, three discrete angle positions are involved. The angle adjustment means 17 engage here before the locking means 18 when the swivel joints 6 are transferred from the adjustment position 7 into the locked position 8.

As shown, the angle adjustment means 17 are formed by elongated pins, which protrude from front head strap 4 and rear head strap 5, wherein the front head strap pins 19 are arranged offset relative to the rear head strap pins 20 in the adjustment position 7 and the front head strap pins 19 and the rear head strap pins 20 engage one in the other in the locked position 8.

Locking means 18 are also provided, which are formed by a toothing, the toothing being opposite the angle adjustment means 17 relative to axis of rotation 10 of swivel joint 6.

Figure 6:
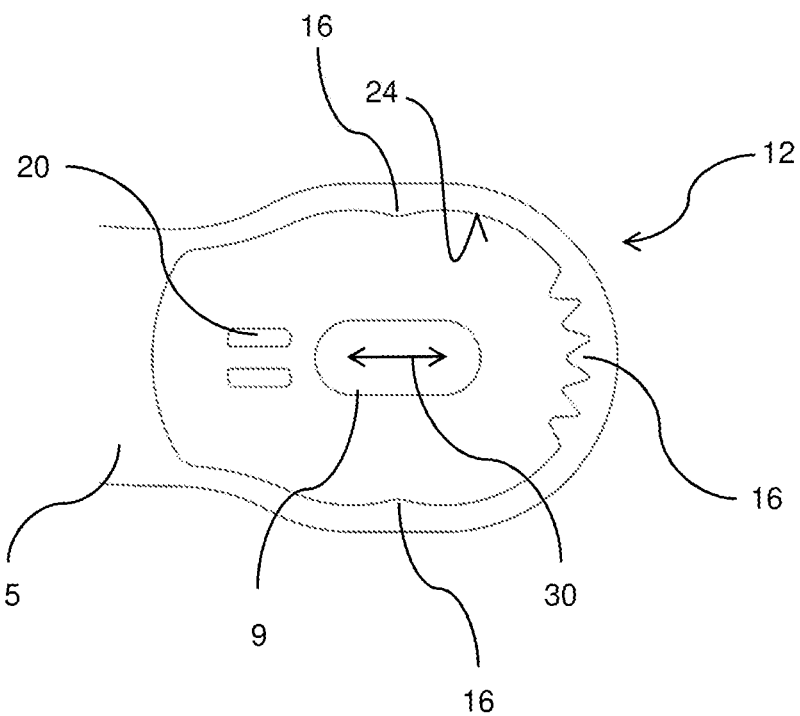
FIG. 6 shows a cut-out view of a rear head strap joint part.

FIG. 6 shows the rear head strap joint part 12 just described on the end of the rear head strap 5 from the side of the front head strap 4.

FIG. 8 shows a respirator hood 29, which is fastened to the head of a wearer 32 by the skull mounting system 1 described above. For this purpose, the skull mounting system 1 is connected to the respirator hood 29 via connection means 33. The connection means 33 are formed in the area of the back of the head by slits into which counter connection means on the respirator hood 29 engage and are positioned to move in the longitudinal direction. Corresponding connection means 33 are shown in FIG. 7.

It is also shown that a corresponding respirator hood 29 preferably has a visor 34, the visor 34 being clear and transparent in the visual field. Visor 34 is connected directly or indirectly to skull mounting system 1 via two additional swivel joints 37 and can be tilted upward via the additional swivel joints 37. It is advantageous here if the transparent part of visor 34 can be easily changed in order to replace it with a new part when it becomes soiled. For this purpose, the transparent part is preferably made from a clear, transparent plastic part.

The respirator hood 29 also has a hood cover 35 that delimits the respirator hood 29 at least in areas relative to the surroundings, so that an overpressure forms in the hood, preventing particles or pollutants from penetrating the internal area of the respirator hood 29 from the outside. For this purpose, the respirator hood 29 is supplied compressed air via a compressed air connection 36.

It should be understood that the present invention has a plurality of different features which may be utilized separately or in various combinations. It is also contemplated that the various features of the invention may be utilized with known features from the prior art. Although specific combination of features have been described herein, it is contemplated that other combinations of features will be apparent to those skilled in the art and will be formed.

Furthermore, although certain applications are described herein, those of ordinary skill in the art will appreciate other applications for the present invention.

In view of the foregoing, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A skull mounting system for headgear, the system comprising:
   a headband that includes:
      a front head strap, which is configured to extend around the front side of the head of the wearer, and
      a rear head strap, which is configured to be situated on the back of the head of the wearer,
   wherein the rear head strap is connected to the front head strap via two swivel joints that allow adjustment of an angle of the rear head strap relative to the front head strap, and
   wherein the swivel joints are at least partially freely rotatable in a corresponding adjustment position and are not rotatable in a corresponding locked position.

2. The skull mounting system of claim 1, wherein each of the swivel joints is transferrable from the adjustment position to the locked position by a relative movement.

3. The skull mounting system of claim 2, wherein the relative movement is a straight-line relative movement of the axis of rotation of the corresponding swivel joint.

4. The skull mounting system of claim 3, wherein the relative movement comprises at least one of the swivel joints sliding in an elongated hole and/or an elongated groove.

5. The skull mounting system of claim 1,
   wherein the rear head strap has a length adjustment means, by means of which the length, and therefore inner circumference, of the headband is adjustable; and
   wherein the rear head strap is configured to be angled downward from the front head strap relative to the head of the wearer.

6. The skull mounting system of claim 1, wherein the swivel joints have an angle adjustment means, by means of which a plurality of angle positions of the rear head strap relative to the front head strap are fixedly defined.

7. The skull mounting system of claim 6, wherein the angle adjustment means are formed by elongated pins, which protrude from the front head strap and the rear head strap, wherein the front head strap elongated pins are arranged in the adjustment position offset relative to the rear head strap elongated pins, wherein the front head strap elongated pins and the rear head strap elongated pins engage one in the other in the locked position.

8. The skull mounting system of claim 6, wherein locking means are provided, which are formed by a toothing, wherein the toothing lies opposite the angle adjustment means relative to the axis of rotation of the corresponding swivel joint.

9. The skull mounting system of claim 8, wherein the angle adjustment means engage before the locking means, when the swivel joints are transferred from the adjustment position to the locked position.

10. The skull mounting system of claim 1, wherein the swivel joints are arranged essentially in the center between a top edge and a bottom edge of the front head strap.

11. The skull mounting system of claim 1, wherein the swivel joints each have a rotary element that protrudes relative to the front head strap and two intersecting recesses on the rear head strap.

12. The skull mounting system of claim 1, wherein the swivel joints each have a rotary element, which has outside toothing on the side opposite rear head strap, and wherein recesses on the side facing the rear head strap have inside toothing that engages with the outside toothing in the locked position and together form locking means.

13. The skull mounting system of claim 1, wherein the swivel joints each have a rotary element, which has a rotary element recess on the side facing the rear head strap, which accommodates part of an angle adjustment means in the adjustment position, wherein at least one side of the rotary element recess forms an end stop for rotational movement of the corresponding swivel joint.

14. A system comprising:
the skull mounting system of claim 1; and
a respirator hood connected to the skull mounting system, wherein the respirator hood includes a visor that is connected to the skull mounting system via two additional swivel joints.

15. A skull mounting system for headgear, the system comprising a headband that includes a front head strap, which is configured to extend around the front side of the head of the wearer, and a rear head strap, which is configured to be situated on the back of the head of the wearer, wherein the rear head strap is connected to the front head strap via two swivel joints, wherein the swivel joints are at least partially freely rotatable in a corresponding adjustment position and are not rotatable in a corresponding locked position, and wherein each of the swivel joints is transferrable from the locked position to the adjustment position by a relative movement of a part of the corresponding swivel joint on the rear head strap in the viewing direction of the wearer.

16. A skull mounting system for headgear, the system comprising a headband that includes a front head strap, which is configured to extend around the front side of the head of the wearer, and a rear head strap, which is configured to be situated on the back of the head of the wearer, wherein the rear head strap is connected to the front head strap via two swivel joints, wherein the swivel joints are at least partially freely rotatable in a corresponding adjustment position and are not rotatable in a corresponding locked position, and wherein the swivel joints each have a securing means which counteracts transfer of the corresponding swivel joint from the adjustment position to the locked position with a securing force that must be applied to overcome the securing means and transfer the swivel joint from the locked position to the adjustment position.

17. The skull mounting system of claim 16, wherein the securing means is in the form of a constriction in an elongated groove or an elongated hole.

18. A method for fastening headgear, the method comprising:
providing the skull mounting system of claim 1 that includes the two swivel joints that connect the rear head strap to the front head strap;
rotating the two swivel joints to adjust the angle of the rear head strap relative to the front head strap according to head shape and/or head size of the wearer of the headgear; and
after rotating the two swivel joints, transferring each of the swivel joints from the adjustment position to the locked position by means of a relative movement of the swivel joint.

19. The method of claim 18, wherein the transfer of the swivel joint from the adjustment position to the locked position comprises reducing the length of the headband.

20. The method of claim 18, wherein the relative movement is a straight-line relative movement.

* * * * *